(12) United States Patent
Godavarty et al.

(10) Patent No.: US 12,144,587 B2
(45) Date of Patent: Nov. 19, 2024

(54) SKIN COLOR INDEPENDENT FLOW-BASED DIFFUSE OPTICAL IMAGING

(71) Applicants: Anuradha Godavarty, Miami, FL (US); Kevin Leiva, Miami, FL (US)

(72) Inventors: Anuradha Godavarty, Miami, FL (US); Kevin Leiva, Miami, FL (US)

(73) Assignee: The Florida International University Board of Trustees, Miami, FL (US)

( * ) Notice: Subject to any disclaimer, the term of this patent is extended or adjusted under 35 U.S.C. 154(b) by 0 days.

(21) Appl. No.: 18/417,405

(22) Filed: Jan. 19, 2024

(65) Prior Publication Data

US 2024/0245301 A1 Jul. 25, 2024

Related U.S. Application Data

(60) Provisional application No. 63/480,669, filed on Jan. 19, 2023.

(51) Int. Cl.
*A61B 5/00* (2006.01)
*A61B 5/083* (2006.01)
*G06T 7/00* (2017.01)

(52) U.S. Cl.
CPC ............ *A61B 5/0086* (2013.01); *A61B 5/083* (2013.01); *A61B 5/445* (2013.01); *A61B 5/742* (2013.01); *G06T 7/0012* (2013.01); *A61B 2576/00* (2013.01); *G06T 2207/20208* (2013.01)

(58) Field of Classification Search
None
See application file for complete search history.

(56) References Cited

U.S. PATENT DOCUMENTS

| | | | |
|---|---|---|---|
| 2010/0210931 A1* | 8/2010 | Cuccia | A61B 5/445 600/328 |
| 2015/0190061 A1* | 7/2015 | Godavarty | G01J 3/0272 600/328 |
| 2020/0386535 A1* | 12/2020 | Brake | G01B 9/02082 |

* cited by examiner

*Primary Examiner* — Jonathan Cwern
(74) *Attorney, Agent, or Firm* — SALIWANCHIK, LLOYD & EISENSCHENK

(57) ABSTRACT

Systems and methods for imaging breath-hold (BH)-induced oxygenation changes in a patient are provided. A non-invasive, non-contact device can be used to image BH-induced oxygenation changes in one or more parts (e.g., foot) of a patient. The patient can hold his or her breath for a set amount of time while imaging is performed using the device, and the imaging can be performed before and/or after the time while the patient is holding his or her breath as well (e.g., during a recovery period). This enables tissue oxygenation based flow correlation independent of melanin concentration (e.g., skin color) of the patient and/or the curvature of the tissue (of the patient) being imaged.

20 Claims, 10 Drawing Sheets

| Case | DFU subject | Status | Side | Week of treatment | DFU Location | Fitzpatrick Grade |
|---|---|---|---|---|---|---|
| 1 | 1 | Healed | Right | 4 | Big Toe (Plantar) | 1 |
| 2 | 2 | Healing | Left | 1 | Midfoot (Post Trans metatarsal amputation) | 2 (Proximal) 5 (Distal) |
| 3 | 2 | Non-Healing | Left | 6 | Midfoot (Post Trans metatarsal amputation) | 2 (Proximal) 5 (Distal) |

FIG. 7

| DFU Subject | Region | Pearson Correlation Coefficient |
|---|---|---|
| Control (Subject 1) | B1 vs B2 | 95.42 % |
| | B1 vs B3 | 95.2 % |
| | B2 vs B3 | 85.5 % |
| 1 (Healed DFU) | B1 vs B2 | 93.9 % |
| | W vs B1 | 95.5 % |
| | W vs B2 | 84.0 % |
| 2 (Week 1 – Healing DFU) | B1 vs B2 | 92.8 % |
| | W vs B1* | 26.1 % |
| | W vs B2* | 31.5 % |
| 2 (Week 6 – Non-Healing DFU) | B1 vs B2 | 84.8 % |
| | W vs B1* | 57.2 % |
| | W vs B2* | 34.3 % |

FIG. 8

| Controls | Dorsum OFI | Sole OFI |
|---|---|---|
| 1 | 36.6 ± 5.5% | 60.2 ± 25.0% |
| 2 | 45.0 ± 12.1% | 59.6 ± 20.5% |
| 3 | 45.0 ± 19.7% | 72.2 ± 22.0% |
| Grand Average | 42.2 ± 12.6% | 64.0 ± 20.5% |

FIG. 9

| DFUs | OFI |
|---|---|
| Healed | 33.4% |
| Healing | 68.4% |
| Non-healing | 9.5% |

FIG. 10

SKIN COLOR INDEPENDENT FLOW-BASED DIFFUSE OPTICAL IMAGING

CROSS-REFERENCE TO RELATED APPLICATION

This application claims the benefit of U.S. Provisional Application Ser. No. 63/480,669, filed Jan. 19, 2023, the disclosure of which is hereby incorporated by reference in its entirety, including all figures, tables, and drawings.

GOVERNMENT SUPPORT

This invention was made with government support under DK125153 awarded by the National Institutes of Health. The government has certain rights in the invention.

BACKGROUND

Approximately one-in-three people with diabetes mellitus (DM) will end up with diabetic foot ulcers (DFUs) during their lifetime. If left untreated or poorly managed, DFUs can lead to amputations, and patients with DFU have an increased 5- and 10-year mortality. The current gold-standard clinical assessment of DFUs includes visual inspection of the wound features (e.g. fissures, granulation, re-epithelialization), sensory feedback (warm to the touch, smell), and wound size measurements across weeks of treatment.

BRIEF SUMMARY

Embodiments of the subject invention provide novel and advantageous systems and methods for imaging breath-hold (BH)-induced oxygenation changes in a patient (e.g., a mammalian patient, such as a human patient). A non-invasive, non-contact device can be used to image BH-induced oxygenation changes in one or more parts (e.g., foot) of a patient. The patient can hold his or her breath for a set amount of time while imaging is performed using the device, and the imaging can be performed before and/or after the time while the patient is holding his or her breath as well (e.g., during a recovery period). The BH stimulus can be performed as either a hold after inhaling air into the lungs (end-inhalation) or exhalation of air from the lungs (end-exhalation). A BH paradigm of a set amount of time (e.g., 60 seconds (s) or 40 s) can be used to induce peripheral vasoconstriction and related oxygenation changes in the patient. (e.g., in the feet of one or more patients) (e.g., one or more control subjects). The imaging can be used to reveal important information about the patient (e.g., hemoglobin concentration in the blood, likelihood of a wound to heal, etc.). Analysis of the imaging can be performed using a processor and a (non-transitory) machine-readable medium (e.g., a computer-readable medium) having instructions stored thereon to perform the imaging analysis steps discussed herein when executed by the processor. The processor and/or the machine-readable medium can be in operable communication with the imaging device. The system can also include a display in operable communication with the processor, the machine-readable medium, and/or the imaging device, and on which results of the imaging and/or the imaging analysis can be displayed.

In an embodiment, a method for performing non-invasive, non-contact imaging on a subject (e.g., a mammalian subject, such as a human subject) can comprise: providing a near-infrared (NIR) optical imager comprising a light unit providing light at at least one NIR wavelength (e.g., a first NIR wavelength), a filter configured to optically filter ambient light and allow only NIR light to pass, and an NIR-sensitive image sensor configured to detect NIR signals reflected from tissue of the subject; utilizing the NIR optical imager to scan tissue of the subject in a non-invasive, non-contact manner while the subject is engaged in a BH phase of a BH paradigm, the BH paradigm comprising an initial rest phase, the BH phase, and a recovery phase; acquiring spatio-temporal diffuse reflected maps based on the reflected NIR signals detected by the NIR-sensitive image sensor (e.g., a camera such as a complementary metal oxide semiconductor (CMOS) camera); generating dynamic maps based on the spatio-temporal diffuse reflected maps; and displaying, via a graphical user interface (GUI) stored on a machine-readable medium in operable communication with the NIR optical imager, the dynamic maps. The filter can be a long-pass filter or a band-pass filter. The NIR signals that the NIR-sensitive image sensor is configured to detect can comprise signals at the first NIR wavelength. The dynamic maps can be independent of a color of skin of the subject and/or tissue curvature of the tissue (of the subject) being imaged. The scanned tissue of the subject can comprise a wound (e.g., a diabetic foot ulcer (DFU)), and the scanned tissue can be on a foot of the subject. The method can further comprise: analyzing the dynamic maps; and determining a likelihood that the wound on the scanned tissue of the subject will heal based on a flow correlation value obtained from analyzing the dynamic maps. The flow correlation value can be a tissue oxygenation-related flow correlation value or a diffuse reflectance-based flow correlation value. The flow correlation value can be, for example, an oxygenation flow index (OFI) of the tissue of the subject. The flow correlation value can be independent of the color of skin of the subject and/or the tissue curvature. The spatio-temporal diffuse reflected maps can be used to generate spatio-temporal tissue oxygenation maps (e.g., during the generating of the dynamic maps). The dynamic maps can comprise oxygenation flow correlation maps, diffuse reflectance-based flow correlation maps, or both. The light unit can providing light at at least two different NIR wavelengths (e.g., at least three different NIR wavelengths, at least four different NIR wavelengths, etc.), and the at least two different NIR wavelengths can be the first NIR wavelength and a second NIR wavelength different from the first NIR wavelength. The NIR signals that the NIR-sensitive image sensor is configured to detect can further comprise signals at the second NIR wavelength. The method can further comprise calculating an OFI of the tissue of the subject based on the oxygenation flow correlation maps. The dynamic maps can comprise at least one of an oxy-hemoglobin (HbO) map, a deoxy-hemoglobin (HbR) map, a total hemoglobin (HbT) map, and an oxygen saturation ($StO_2$) map for a region of interest (ROI) of the tissue of the subject. The method can further comprise extracting time-varying hemoglobin concentration profiles (e.g., HbO, HbR, and/or HbT) from the dynamic maps. The acquiring of the spatio-temporal diffuse reflected maps can comprise: coregistering the reflected NIR signals to minimize motion artifacts; and using modified Beer-Lambert's Law to generate the spatio-temporal diffuse reflected maps based on the coregistered reflected NIR signals. Each of the first wavelength and the second wavelength can be in a range of, for example, from 650 nanometers (nm) to 950 nm. For example, the first wavelength can be 682 nm, and/or the second wavelength can be 826 nm. The light unit of the NIR optical imager can be a light-emitting diode (LED) light unit. The NIR optical imager can further comprise an LED driver configured to multiplex light from the LED light unit. The method can further comprise multiplexing the first wavelength (and the second wavelength (if present)) at a first temporal frequency (and a second temporal frequency, respectively). Each of the first temporal frequency and the second temporal frequency can be in a range of, for example, 0.5 Hertz (Hz) to 100 Hz. The first temporal frequency can be the same as the second temporal frequency (or can alternatively be different from the second temporal frequency). The breath hold phase can be an end-exhalation breath hold phase or an end-inhalation breath hold phase. The BH phase can be at least 10 seconds (s) (e.g., any value or range contained within the range of 5 s to 100 s, such as 20 s, at least 20 s, or about 20 s), the initial rest phase can be at least 10 s (e.g., any value or range contained within the range of 5 s to 100 s, such as 20 s, at least 20 s, about 20 s, 40 s, at least 40 s, or about 40 s), and the recovery phase can be at least 10 s (e.g., any value or range contained within the range of 5 s to 100 s, such as 20 s, at least 20 s, about 20 s, 40 s, at least 40 s, or about 40 s). The utilizing of the NIR optical imager to scan the tissue of the subject can be performed while the subject is engaged in at least a portion of the recovery phase of the BH paradigm and/or at least a portion of the initial rest phase of the BH paradigm.

In another embodiment, a system for performing non-invasive, non-contact imaging on a subject (e.g., a mammalian subject, such as a human subject) can comprise: an NIR optical imager (which can be referred to as a NIROS); a (non-transitory) machine-readable medium (e.g., a (non-transitory) computer-readable medium) in operable communication with the NIR optical imager and having a GUI stored thereon; and a processor in operable communication with the machine-readable medium. The NIR optical imager can have any or all of the features described herein (such as in the previous paragraph). The system can be configured to perform any of the steps described herein (such as in the previous paragraph). The system can further comprise a display in operable communication with the machine-readable medium and upon which the GUI (and therefore the spatio-temporal diffuse reflected maps) is displayed. The NIR optical imager can be a standalone device, a smartphone device, or integrated smartphone device.

BRIEF DESCRIPTION OF DRAWINGS

In FIG. 2A, a region of interest encompassing the imaged foot tissue region was manually selected to remove the background region outside the foot. FIG. 2B shows the hemoglobin concentration changes at each pixel extracted across time. FIG. 2C shows that the Savitzky-Golay filter was applied to each two-dimensional (2D) pixel location across time to smoothen the signal while preserving the trend. FIG. 2D shows that the average of the filtered signals was calculated to characterize the breath-hold induced hemoglobin concentration changes by subject. The average signal was initialized and normalized as the percent change with respect to breath-hold onset, where "H" represents high and "L" represents low concentrations for the normalized hemoglobin-based parameter. Measurements from t=40 s-120 s were further evaluated to assess the breath-hold induced hemoglobin changes. FIG. 2E shows a plot of percent change versus time (in s) showing the grand average, or average of the average hemoglobin concentration signals, being used to characterize the breath-hold induced response for each subject, each imaged side of the foot, and each hemoglobin concentration parameter.

FIG. 7 shows a table of details of two DFU cases assessed for effect of skin color.

FIG. 8 shows a table of Pearson's correlation coefficients calculated between ROIs for one control case and three DFU cases. Asterisks indicate cases with low correlation coefficients between wound and backgrounds.

FIG. 9 shows a table of average of the oxygenation flow index (OFI) by subject and imaged foot side.

FIG. 10 shows a table of OFI in DFU cases.

DETAILED DESCRIPTION

Figure 1:
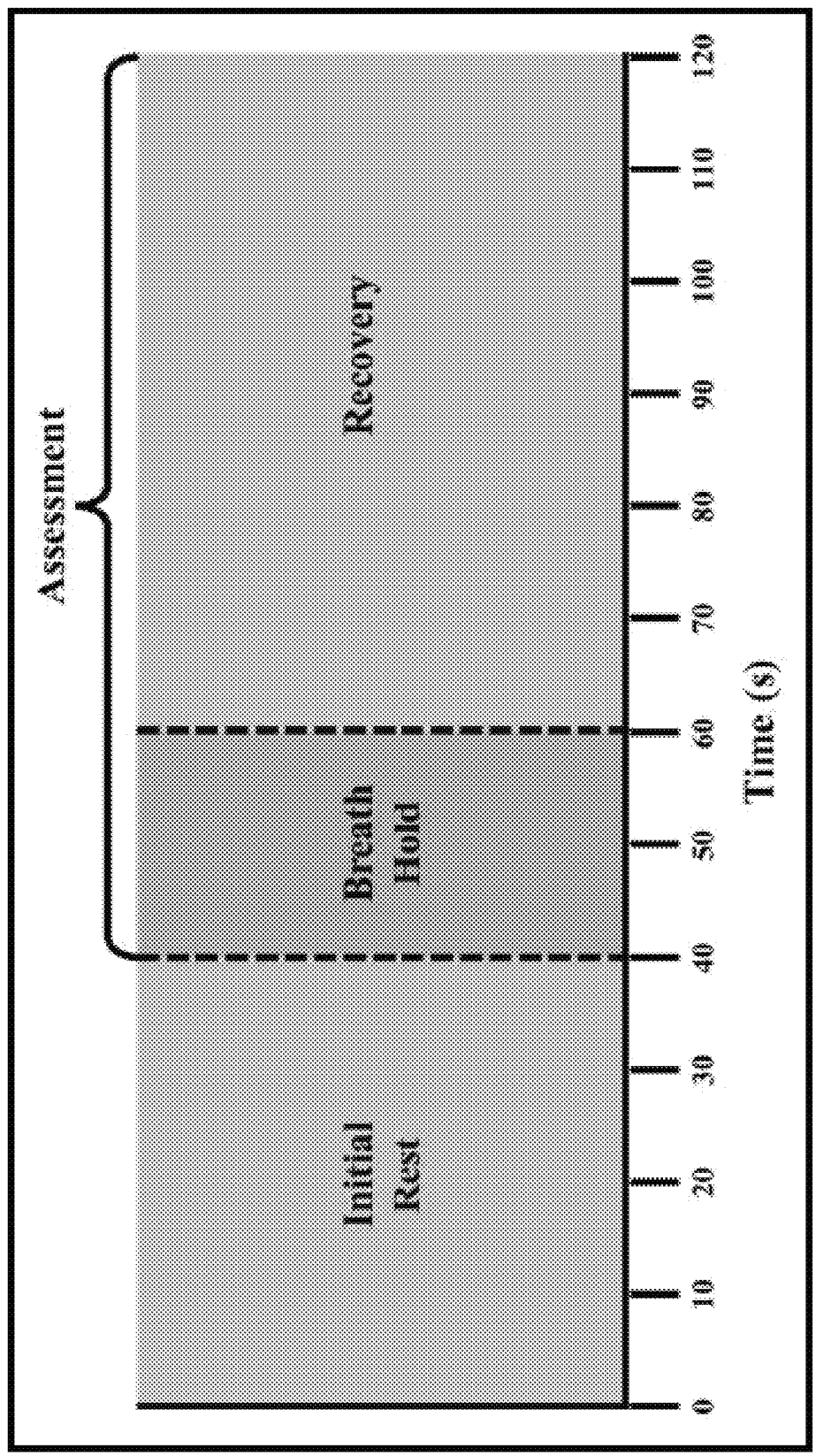
FIG. 1 shows a 120-second (s) long breath-hold paradigm, which includes three phases: initial rest (t=0 s-40 s), end exhalation breath-holding (t=40 s-60 s), and a recovery phase (t=61 s-120 s). Tissue oxygenation changes were assessed during and after the breath-hold (recovery) phase.

Embodiments of the subject invention provide novel and advantageous systems and methods for imaging breath-hold (BH)-induced oxygenation changes in a patient (e.g., a mammalian patient, such as a human patient). A non-invasive, non-contact device can be used to image BH-induced oxygenation changes in one or more parts (e.g., foot) of a patient. The patient can hold his or her breath for a set amount of time while imaging is performed using the device, and the imaging can be performed before and/or after the time while the patient is holding his or her breath as well (e.g., during a recovery period). The BH stimulus can be performed as either a hold after inhaling air into the lungs (end-inhalation) or exhalation of air from the lungs (end-exhalation). A BH paradigm of a set amount of time (e.g., 60 seconds (s) or 40 s) can be used to induce peripheral vasoconstriction and related oxygenation changes in the patient. (e.g., in the feet of one or more patients) (e.g., one or more control subjects). The imaging can be used to reveal important information about the patient (e.g., hemoglobin concentration in the blood, likelihood of a wound to heal, etc.). Analysis of the imaging can be performed using a processor and a (non-transitory) machine-readable medium (e.g., a computer-readable medium) having instructions stored thereon to perform the imaging analysis steps discussed herein when executed by the processor. The processor and/or the machine-readable medium can be in operable communication with the imaging device. The system can also include a display in operable communication with the processor, the machine-readable medium, and/or the imaging device, and on which results of the imaging and/or the imaging analysis can be displayed.

Tissue oxygenation measurements obtained from diffuse optical imaging are intensity-dependent measurements that can be impacted by varying skin colors (or melanin concentrations). Embodiments of the subject invention provide systems and techniques to minimize or remove the effect of varying skin colors during diffuse optical imaging studies using a stimulus that also allows differentiation between diseased and normal tissues based on differences in flow-patterns. An innovative BH stimulus can induce peripheral oxygenation flow changes and measured using an imaging device (e.g., a near-infrared spectroscopy (NIRS)-based imaging device). While certain hyperspectral and multi-spectral imaging approaches can measure the effective amount of oxygen already present in the tissue, they are unable to assess how the vasculature responds to an oxygenation altering stimulus as observed by the gold-standard transcutaneous oximetry (TCOM). In embodiments of the subject invention, a mammalian BH mechanism induces vasoconstriction in the limb, altering blood flow and oxygenation flow changes in and around the wound site.

Oxygen is a vital component for wound healing. In the presence of microvascular dysfunction, the wound healing process can be negatively impacted via restriction of the oxygenated blood flow to the site. Patients afflicted with cardiometabolic diseases, such as diabetes mellitus (DM), are predisposed towards microvascular insufficiencies and may experience stagnated healing of their injured tissues. TCOM-based devices are the gold-standard approach in assessing the wound healing status of diabetic foot ulcers (DFUs). TCOM is a non-invasive imaging approach that measures the partial pressure of oxygen diffused throughout the skin at discrete point locations around the wound site. That is, it measures the oxygen-delivering capacity of the vascular system.

TCOM devices utilize heating elements to induce tissue heating (e.g., 44° C. or about 44° C.) as a stimulus to measure the partial pressure of oxygen under the skin. The dermal layer of the skin includes a rich network of blood containing vessels that are highly sensitive to thermal stress. The upper papillary layer of the dermis is home to a large quantity of capillary loops used for thermal regulation. In response to increased body temperature, the capillary loops dilate to increase blood flow for improved heat transfer with the external environment. Tissue heating caused by the TCOM device induces vasodilation in the capillary loops to better measure the amount of oxygen present in the assessed tissue.

TCOM is a time-consuming procedure (e.g., 30 minutes, about 30 minutes, or at least 30 minutes) and is performed as a contact-based imaging approach. Due to the contact imaging nature of the TCOM approach, it only provides information in the peri-wound at discrete point locations and not the entire wound bed and its surroundings. TCOM also requires additional equipment to increase the temperature around the wound, as a stimulus, to determine the partial pressures of oxygen. Thus, the applicability of TCOM as a bed-side tool to assess all chronic DFUs during each visit or treatment is pragmatically challenging. There is a need for alternative non-invasive imaging techniques that can image the entire wound bed and its surroundings for these oxygenation changes to provide similar information to that of TCOM, but without the additional equipment and time-intensive procedures.

Various non-invasive optical imaging technologies have been developed to assess the tissue oxygenation distribution in and around the wound region. These include non-contact hyperspectral imaging (HSI) and multi-spectral imaging (MSI) devices, as well as contact-based near-infrared spectroscopy (NIRS) devices. HSI and MSI obtain two-dimensional (2D) maps of tissue oxygenation, via hemoglobin-based parameters, and compare them across weeks of treatment to assess the healing potential. While HSI and MSI are capable of measuring the effective amount of oxygen already present in the tissue, unlike the gold-standard TCOM, they are unable to assess how the vasculature responds to an oxygenation altering stimulus.

Embodiments of the subject invention provide hand-held near-infrared spectroscopy (NIRS) based imaging devices and near-infrared optical scanners (NIROSs). The NIROS can provide non-contact spatial-temporal oxygenation monitoring as an indirect measure of perfusion. The imaging approach utilizes an innovative breath-hold (BH) paradigm as a stimulus to induce oxygenation changes to the wound site. It is thought that the mammalian BH mechanism induces vasoconstriction in the limb, altering blood flow and oxygenation. The characterization of BH-induced oxygenation changes can be used as a stimulus to assess the ability of peripheral vasculature to respond to an oxygenation demand in diseased tissue models such as DFUs.

All mammals possess an innate series of physiological mechanisms to conserve oxygen during periods of apnea. BH mechanisms prioritize brain oxygenation by triggering a series of cardiovascular changes to maintain cerebrovascular flow. Due to the simplicity in implementing BH mechanisms, they can be used as a vasodilative stimulus in brain imaging. These mechanisms require as little as 10 seconds of breath-holding to produce a blood oxygen level dependent (BOLD) signal. Oxygen conservation is achieved through a combination of BH-induced bradycardia and peripheral vasoconstriction. The extent of how much each physiological mechanism contributes to the conservation effect is affected by physiological factors (e.g., fitness, initial lung capacity), environment (wet/dry), and physical state (resting/exercising) of the participants.

Independent of any bradycardic response to breath holding, vasoconstrictive mechanisms are engaged to reduce blood flow to the skin and muscles of the periphery. Skin blood flow can be reduced by 40% and that muscle oxygenation decrease can be observed as early as 10 seconds under BH conditions. While the exact mechanism of the vasoconstrictive effect is not completely certain, the reduced blood flow to the limbs is due to reduced compliance in peripheral vasculature as opposed to a reduction in perfusion pressure. Using a 20-sec breath-hold based stimulus, synchronous, or correlated, tissue oxygenation flow patterns have been observed in control subjects (with no DFUs) and asynchronous, or lesser correlated, flow patterns have been observed in DFU cases (see Leiva et al., "Breath-Hold Paradigm to Assess Variations in Oxygen Flow in Diabetic Foot Ulcers Using a Noncontact Near-Infrared Optical Scanner," Advances in Wound Care 8(8), 386-402, 2019, doi: 10.1089/wound.2018.0922; which is hereby incorporated by reference herein in its entirety).

Embodiments of the subject invention optimize and establish the BH paradigm as the stimulus to assess the adequacy of oxygenation flow (e.g., via control subjects). This can be systematically carried out via, for example, in vivo studies on control subjects to: (1) validate that BH induces peripheral tissue oxygenation changes; and (2) determine the typical oxygenated flow patterns in control subjects on the dorsal and sole side of the foot. A preliminary assessment of the differences in BH-induced oxygenation flow changes can also be performed between control subjects with a healed DFU, healing DFUs, and non-healing DFU case with differing melanin concentrations.

Figure 11:
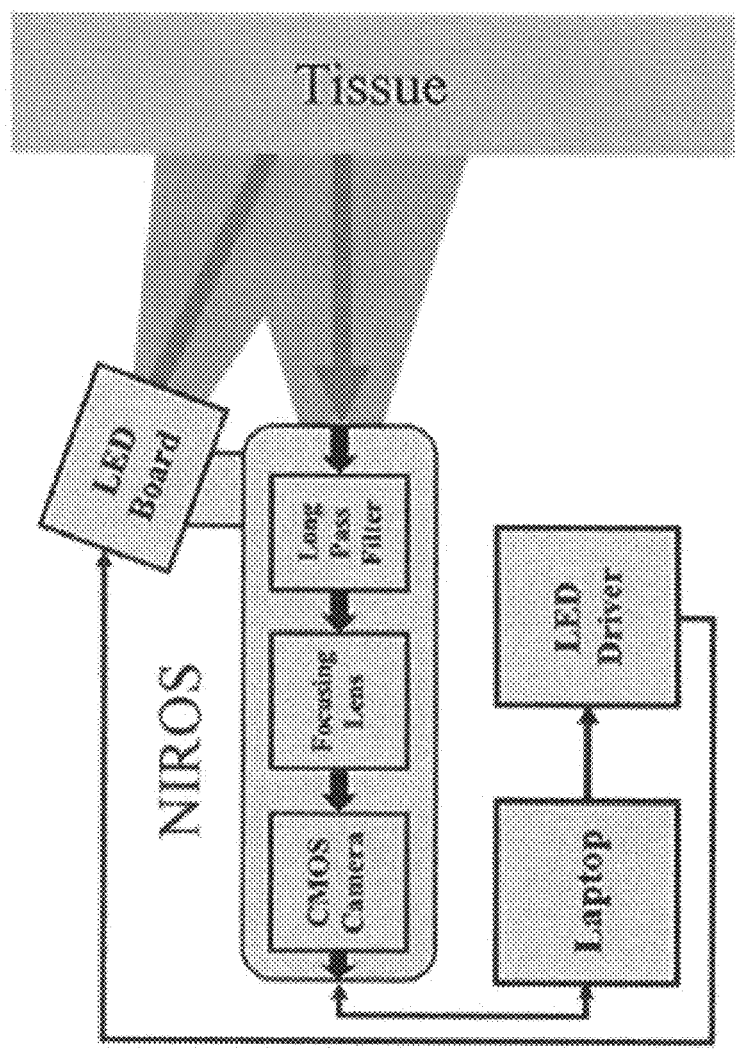
FIG. 11 shows a schematic of a near-infrared optical scanner (NIROS) that can be utilized for noncontact imaging of control and DFU subjects, according to an embodiment of the subject invention. Arrows indicate the flow of information throughout the NIROS components, including an image sensor (e.g., a camera such as a complementary metal oxide semiconductor (CMOS) camera), a light source (e.g., a light driver, such as a light emitting diode (LED) driver), an LED board, a focusing lens, a filter (e.g., a long pass filter), and a computing system (e.g., a laptop).

Referring to FIG. 11, in an embodiment, a continuous-wave NIROS can be used to conduct non-contact imaging (e.g., of the foot of a patient (e.g., a mammalian patient such as a human patient)). NIROS utilizes dual-wavelength (e.g., 682 nanometers (nm) and 826 nm, though embodiments are not limited thereto) near-infrared (NIR) lights (e.g., light-emitting diode (LED)) or light packages. The NIR source light can be diffused (e.g., via a diffuser sheet) prior to illuminating the tissue regions across a wide area. The diffusedly reflected NIR signals from the tissue passes through a long pass filter (e.g., a 645-nm long pass filter, such as LP 645, MidOpt) before being detected by a NIR sensitive camera (e.g., a complementary metal oxide semiconductor (CMOS) camera, such as IDS, Germany). A driver, such as an LED driver (e.g., a custom LED driver) can be used to multiplex each wavelength at a temporal frequency with a set optical power at the source end (e.g., a 1 Hertz (Hz) temporal frequency with 32 milliwatts (mW) of optical power at the source end). The driver can be optimized such that the source intensity and wavelength are stable during the dynamic imaging sessions for a set time (e.g., up to 8 minutes). A graphical user interface (GUI) (e.g., a Matlab-based GUI) can be used to automate spatio-temporal acquisition of diffusedly reflected signals from the NIROS device. Additional details of the NIROS device can be found in Leiva et al., Advances in Wound Care 8(8) (supra.).

In embodiments of the subject invention, the breath-hold stimulus can be performed as either a hold after inhaling air into the lungs (end-inhalation) or exhalation of air from the lungs (end-exhalation). Even though the description herein focuses largely on end-exhalation, this is for exemplary purposes only and should not be construed as limiting.

FIG. 1 shows a 120-second (s) long BH paradigm, which includes three phases: initial rest (t=0 s-40 s), end exhalation breath-holding (t=40 s-60 s), and a recovery phase (t=60 s-120 s). Tissue oxygenation changes were assessed during and after the breath-hold (recovery) phase. Diffuse reflectance measurements in response to the BH paradigm can be acquired from each subject (e.g., each subject's dorsal and/or sole of a foot (e.g., the left foot or the right foot)). As variation in the BH-induced oxygenation changes may exist within each subject, repeated measure (e.g., three repeated measures) of BH-induced oxygenated flow changes can be acquired from both sides of the foot during a single visit. A rest period (e.g., a 15-minute rest period) can be provided across the repeated measures acquired from each side of each subject's foot (dorsum and/or sole). Subjects can be, for example, seated on a chair in the fowler position. Prior to imaging studies, the foot of each subject can be positioned onto a custom mount to minimize motion artifacts during the imaging (e.g., the 120-sec imaging study). Fiducial markers can be placed distally on either side of the subject's foot for spatial referencing. Imaging can be performed in a dark room with the device positioned a distance (e.g., 15 centimeters (cm) or about 15 cm) away from the imaged foot. A uniformly diffusing calibration sheet (e.g., a disposable white cardstock) can be used to capture the reference NIR signal across the imaged area (e.g., at both 682 nm and 826 nm wavelengths) prior to each imaging study.

A graphical user interface (GUI) (e.g., a Matlab-based GUI) can be used to perform image analysis of the diffusely acquired NIR signals. The various steps in the image analysis process can include: coregistering the time-varying diffusely reflected NIR images to minimize motion artifacts; obtaining the spatio-temporal tissue oxygenation maps; extracting the time-varying hemoglobin concentration profiles; determining the oxygenation flow correlation maps; and/or calculating the oxygenation flow index (OFI).

Step 1: Coregistering the time varying NIR images: Prior to evaluating the hemoglobin concentration maps from the dual wavelength diffusedly reflected NIR images, each image set can be visually inspected for motion artifacts. The motion artifacts can be corrected (or minimized) via an intensity-based coregistration algorithm. The coregistration technique can automatically rotate and/or translate the NIR images to align with the NIR image acquired at the first time point during each imaging session. The geometric transformations of the NIR tissue images can be accounted for in the reference images acquired using the calibration sheet.

Step 2: Spatio-temporal tissue oxygenation maps: The modified Beer-Lambert's Law (mBLL) can be utilized to calculate the spatio-temporal maps of the effective hemoglobin-based oxygenation using the coregistered diffusedly reflected NIR images of the tissue and calibration sheet. The detailed analysis to obtain tissue oxygenation maps is described in Leiva et al., Advances in Wound Care 8(8) (supra.). Spatio-temporal oxygenation maps can be calculated in terms of effective oxy-($\Delta$HbO), deoxy-($\Delta$HbR), total hemoglobin ($\Delta$HbT), and oxygen saturation ($\Delta$StO$_2$) for each case. These oxygenation maps can be calculated for each repetition study on the dorsum and sole sides of the foot in each subject (excluding the toes).

Figures 2A, 2B, 2C, 2D, 2E:
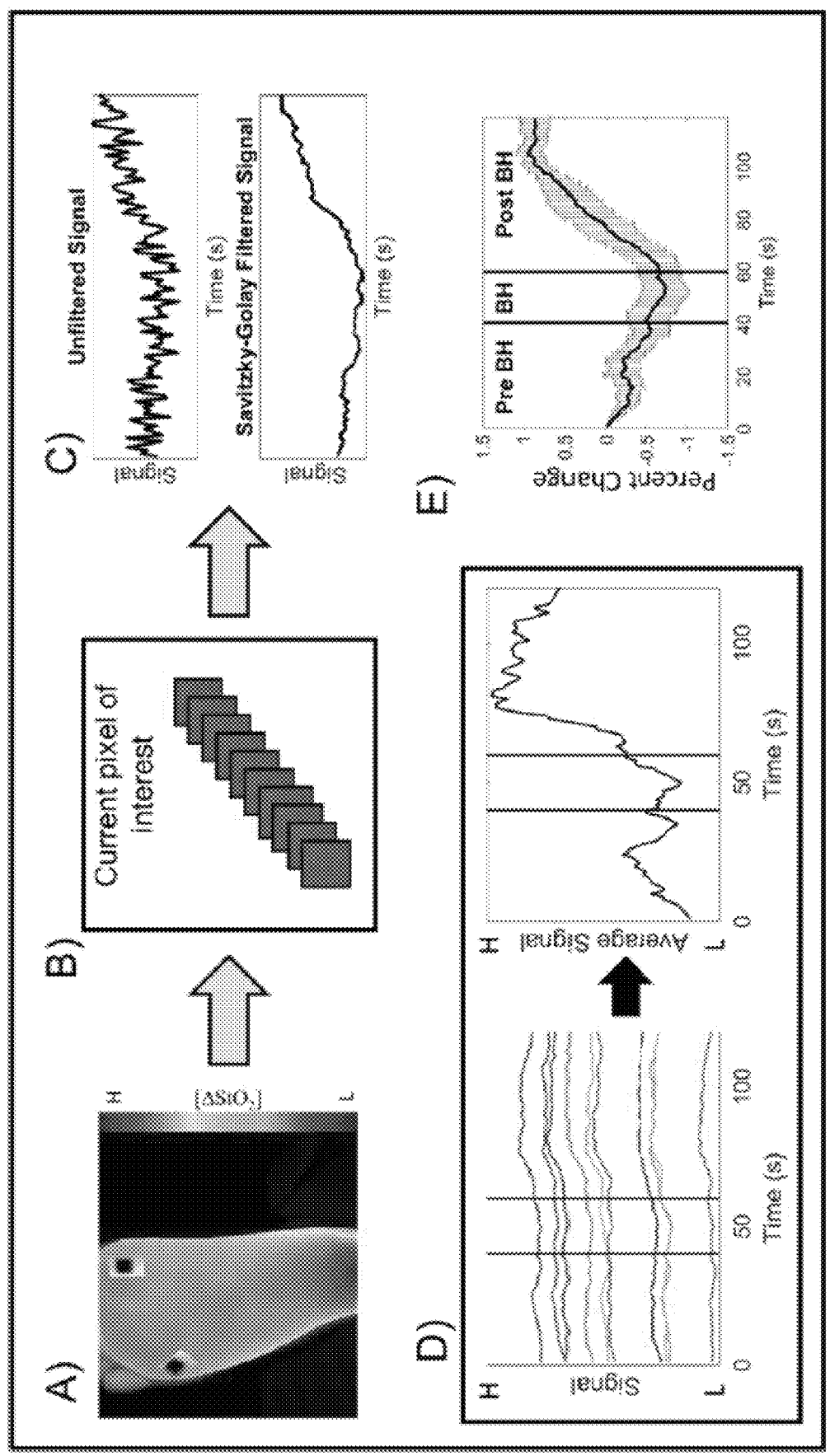
FIGS. 2A-2E show schematic view of the image analysis process to calculate the time-varying hemoglobin concentration profiles for an arbitrary subject and hemoglobin-based parameter, according to an embodiment of the subject invention.

Step 3: Time-varying hemoglobin concentration profiles: In each spatio-temporal map, the region of interest (ROI) can be defined as the imaged tissue region within the foot. The non-tissue background can be segmented out from the spatio-temporal maps, and the changes in tissue oxygenation can be assessed across the entire imaged region of the foot (as shown in one sample subject in FIG. 2A). The time varying effective hemoglobin-based concentration changes can be extracted at each pixel location of the 2D spatial map (see FIG. 2B). The Savitzky-Golay filter can be applied at each pixel location across time to smoothen the signal while preserving the signal trend (see FIG. 2C). The time-varying hemoglobin concentration profiles acquired across each pixel can be averaged across the entire ROI (see FIG. 2D). The averaged time-varying hemoglobin concentration profile from the onset time point of the breath-hold paradigm can be considered for further analysis (i.e., t=40 s onwards). This profile can be initialized and normalized with respect to first time point of breath-hold onset to obtain the percent change in oxygenation signal. The average and standard error of the breath-hold induced hemoglobin concentration profile (from t=40 s-120 s) can be calculated from the grand average, or the average of the average, hemoglobin concentration signal across all subjects (e.g., three subjects) and repetitions (e.g., three repetitions) for a given side of the imaged foot and parameter (see FIG. 2E).

Step 4: Oxygenation flow correlation maps: The oxygenated flow correlation maps can be developed to assess synchrony or asynchrony in oxygenation changes over the imaged region. The stimulus induced oxygenated flow can be compared against a reference oxygenated flow signal across each 2D spatial pixel location that varied with time. The oxygenated flow correlation maps can be generated using the time-varying $\Delta StO2$ spatio-temporal hemoglobin concentration maps (see Leiva et al., Advances in Wound Care 8(8) (supra.)). The oxygenated flow synchrony at each pixel location was calculated via linear correlation analysis to calculate the Pearson's correlation coefficient (PCC). The PCC was calculated as given in Equation (1):

$$PCC(x, y) = \frac{\sum_{i=1}^{n}(X - \overline{X})(Y_i - \overline{Y})}{\sqrt{\sum_{i=1}^{n}(X_i - \overline{X})^2 (Y_i - \overline{Y})^2}} \quad (1)$$

where $\overline{X}$ is the mean value of the reference signal across time, $X_i$ is the value of the reference signal at the nth time point, $\overline{Y}$ is the mean value of $\Delta StO_2$ of the Yth pixel across time, and $Y_i$ is the $\Delta StO_2$ value of the $Y^{th}$ at the nth time point. The output is a 2D Pearson's correlation map that ranges from $-1$ (negatively correlated flow) to $+1$ (positively correlated flow). Each pixel location can be viewed as an individual correlation assessment of hemoglobin-based oxygenation changes at that pixel location against the reference signal. Oxygenated flow correlation maps can be calculated for controls subjects and DFU cases in a current study. The average $\Delta StO_2$ across each 2D map can be used as the reference signal for control subjects since they did not possess wounds.

For DFU subjects, the $\Delta StO_2$ from an ROI in the background region (away from the wound site) can be used as a reference signal. The ROI-based approach allows for direct comparison of background perfusion changes between the wound and peri-wound region.

A preliminary analysis observed that distinct oxygenation flow changes were observed during the 20 s of breath-holding (t=40 s-60 s), and within the first 20 s of the recovery, or post-breath-hold phase (t=60 s-80 s). Hence, flow correlation maps can be generated using only this 40 s range of BH-induced changes.

Figure 3:
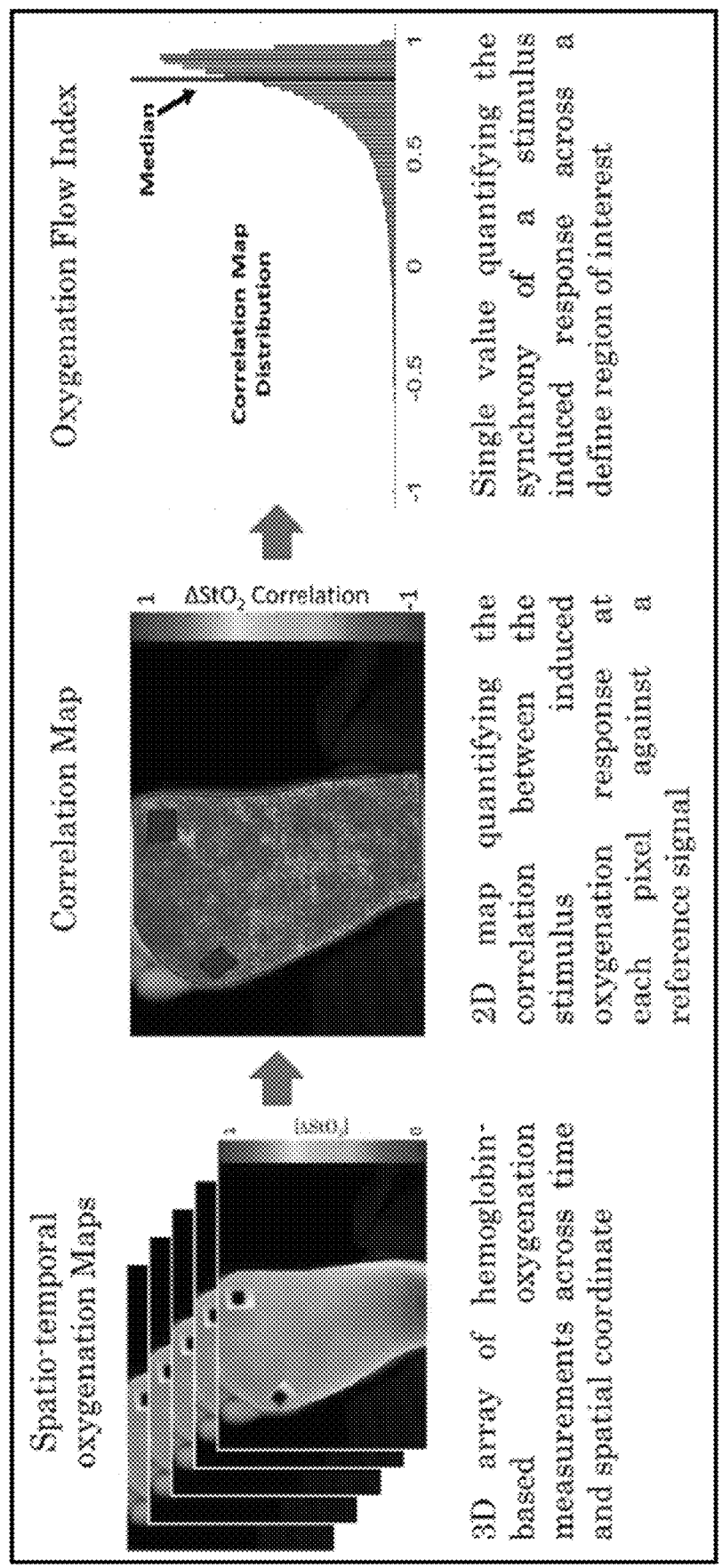
FIG. 3 shows a summary block diagram detailing the steps for calculating the oxygenation flow index (OFI) values, according to an embodiment of the subject invention.

Step 5: Calculation of the OFT: The median value of the Pearson's correlation coefficient distribution in each map can be determined. The extracted median value of the correlation coefficient distribution can be used as a measure to assess the overall extent of synchrony, or asynchrony, in each subject and imaged side of the foot (dorsum or sole) (as shown in FIG. 3). Using the median of the correlation coefficient distribution instead of the average of the distribution provides insight into the central tendency of the correlation distribution, even in potentially skewed distributions. Herein, the median value of the correlation coefficient distribution in each map is referred to as the OFI.

The hemoglobin concentration profiles in terms of $\Delta HbO$, $\Delta HbR$, $\Delta HbT$, and $\Delta StO_2$ across the 20 s of breath-holding (t=40 s-60 s) and the 60 s of post breath-hold (t=60 s-120 s) can be calculated for each subject. The average profile for each of these hemoglobin concentrations can be calculated across all control subjects and repetitions, for each side of the imaged left foot and given in FIGS. 4A-4H.

An increase in $\Delta HbR$ was observed during the 20 s breath-hold phase. There was an increase in $\Delta HbO$, $\Delta HbT$, and $\Delta StO_2$ end of the 20 s breath-hold and in the post-breath-hold (recovery) phase in the foot's dorsum and sole. On the contrary, the $\Delta HbR$ dropped during the recovery phase.

The trend was increased oxyhemoglobin and oxygen saturation post breath-hold, and this increase in oxyhemoglobin and oxygen saturation was distinct within the first 20 s of the recovery period itself. Hence, the correlation maps can be generated using only the 40 s timespan encompassing the 20 s recovery period along with the 20 s breath hold period. This reduces the overall computation power/time (improving the performance of the device performing the computation) while still generating flow correlation maps that include the changes in oxygenation in response to the breath-hold stimulus.

When using optical imaging modalities that measure tissue oxygenation (such as NIRS) from the skin's surface, light is significantly attenuated with an increase in melanin concentration in the epidermis. It is essential to account for this melanin-related attenuation (in the epidermis) to evaluate the changes in tissue oxygenation in the dermis and lower layers of the skin. In embodiments of the subject invention, the tissue oxygenation changes can be dynamically measured in response to a BH stimulus, which is not expected to change the melanin concentration, but the underlying tissue oxygenation. Further, the observed oxygenated flow changes in controls indicated that breath-holding may be suitable as a stimulus to assess the perfusion to wounds.

Spatial variations in skin pigmentation are more obvious in wounds as they heal. A feasibility study was performed on two DFU subjects in a UM-IRB (University of Miami-Internal review board) approved study at the University of Miami Wound Care Center (see K. Leiva et al., "Comparison of oxygenated flow patterns in diabetic foot ulcers subjects and controls in response to breath-holding," in Optical Biopsy XX: Toward Real-Time Spectroscopic Imaging and Diagnosis, R. R. Alfano, S. G. Demos, and A. B. Seddon, Eds., p. 25, SPIE, San Francisco, United States, 2022, doi:10.1117/12.2610362; which is hereby incorporated by reference herein in its entirety). This feasibility study was performed to assess if (i) breath-holding could induce oxygenated flow changes in diabetic foot ulcers apart from control subjects, and (ii) if variations in skin color impacts the dynamically changing tissue oxygenation measurements in response to the breath-hold stimulus. The recruited DFU subjects demonstrated a range of skin color (corresponding with Fitzpatrick grades of 1 to 5). The first recruited DFU subject (subject 1 in the table in FIG. 7) was a healed DFU case (as clinically assessed). The second subject (subject 2 in the table in FIG. 7) was a post trans metatarsal amputation case imaged twice across weeks. During the two timepoints of imaging, the wound was clinically assessed as healing and non-healing. From a prior amputation, subject 2 had two varying skin colors around the DFU. The details of the recruited DFU subjects are listed in FIG. 7.

Both DFU subjects were imaged using the same breath-hold paradigm as that in the controls. The tissue oxygenation changes in response to breath-hold were compared across the DFU cases and in comparison to a control case in FIGS. 5A-5D. A 50×50-pixel ROI was selected over the (former) wound (W) and two background (B) tissue regions. For the second DFU subject, one ROI was selected in the proximal and distal end of the mid-foot to assess tissue oxygenation changes from lighter (B1) and darker (B2) skin regions, respectively. For the control case with no wounds, three ROIs were selected across the entire foot (B1, B2, and B3).

The hemoglobin concentration profiles (in terms of $\Delta StO_2$) in response to the breath-hold is shown for all imaged cases and the selected ROIs. The pairwise Pearson's correlation coefficient was calculated between ROIs within each case and provided in the table in FIG. 8.

All DFU cases demonstrated an increase in $\Delta StO_2$ following breath-hold cessation like the sample control case (see FIGS. 5A-5D). However, the time-varying response to breath-hold differed between the two DFU cases. It was further observed that the Pearson's-based correlation was high between $\Delta StO_2$ signals acquired from background tissue regions (i.e., B1 vs B2, B2 vs B3 and B1 vs B3) across cases (FIG. 8).

Regardless of healing and disease status of the imaged tissue, all cases demonstrated strong correlated between their respective background regions (>84%). Furthermore, in healing and non-healing DFU cases from subject 2, the lighter (Fitzpatrick grade 2) and darker (Fitzpatrick grade 5) backgrounds ROIs were strongly correlated (>84%). This demonstrates that oxygenation flow patterns are synchronous, independent of the skin colors in the background regions. With regards to oxygenation changes in the wound, of the healing and non-healing DFU cases from subject 2, the wound was only weak to moderately correlated (26-57%) to the background region.

Hemoglobin concentration profiles provided insight into the oxygenation changes at a given tissue location but did not provide in-depth insight in the oxygenated flow changes across a 2D region of tissue. In the presence of a wound, the breath-hold response may be altered due to complications or the wound undergoing healing. In order to assess the synchrony of breath-hold induced oxygenation changes across the foot, correlation maps were calculated for the cases in FIGS. 5A-5D.

Oxygen saturation-based correlation maps were calculated for all control cases and the three DFU cases (across the two DFU subjects) and given in FIGS. 6A-6D. Flow correlation maps were generated using only the oxygen saturation-based hemoglobin parameter. Oxygen saturation (or tissue oxygenation) was chosen because it is a potentially good indicator of wound healing. In DFU subjects, flow patterns may differ between uninjured and wounded tissue regions. For the DFU subjects, the correlation maps were generated using a ROI-based reference signal selected from a region far away from the ulceration (i.e., the background) as the reference signal in Equation (1). An ROI-based reference signal can be used to select an uninjured region as a baseline for comparing the flow synchrony. From each correlation map, several sub-ROIs were selected. The average correlation coefficient was calculated for each sub-ROI to evaluate the flow synchrony at various points of the foot.

Referring to FIGS. 6A-6D, the control case was positively correlated across the entire sole of the foot. In addition, the whole foot had a similar degree of correlation (i.e., highly positively correlated across the foot) with respect to the average $\Delta StO_2$-based reference signal. Visually, this could be inferred from the primarily red coloration of the correlation map. The healed and healing DFU were both positively correlated across the foot, similar to the control case, but to a lesser degree. In the healed DFU, the distal and proximal sub-ROIs of the foot was more positively correlated than the middle sub-ROI (2%). In the healing DFU, the proximal (heel direction) sub-ROI was more correlated than the distal end. The wound region was also weakly correlated (7%) as compared to the background tissue.

The non-healing DFU case, however, had visually apparent negatively correlated (asynchronous) oxygenated flow in and around the DFU. The non-healing DFU correlation map had a region of negatively correlated tissue (correlation value of −40.8% to −49.8%) in and around the wound region, indicating asynchronous oxygenated flow and an overall low synchrony in the oxygenated flow response. Overall, the extent of (a)synchrony in the oxygenated flow may differ between healing and non-healing DFUs. While assessing the PCC at distinct regions can provide insight into how synchronous the oxygenated flow changes were, they do not adequately describe the overall flow synchrony across the foot.

The overall synchrony of the oxygenated flow across the imaged tissues was determined using the OFI. The table in FIG. 9 lists the average and standard deviation of the OFIs calculated for each control subject across repetitions. OFIs were further calculated for the dorsum and sole of the foot to identify any potential differences in overall flow synchrony. All control subjects had positively correlated flow (or synchronous flow) in both the dorsum (~42%) and sole (~64%) of the foot. In controls, the sole side of the foot had higher OFI values than the dorsum side.

The OFIs of the healed and healing DFU cases are given in the table in FIG. 10. The DFU subjects performed the breath-hold paradigm only once during their weekly clinical visit (unlike the 3 repetitions possible in control subjects). It was observed that the OFIs in healing and healed DFU case was similar to that observed in controls, unlike the non-healing DFU case. The flow correlation maps and OFI assessment across the different cases is a feasibility study, though an extensive correlation analysis across multiple DFU cases could also be performed in which flow correlation-based thresholds can be developed to differentiate healing versus non-healing DFUs from the spatio-temporal tissue oxygenation maps in response to the breath-hold paradigm.

Breath-holding invokes cerebrovascular and cardiovascular changes to maintain oxygen supply to the brain and core functions. Due to this, BH paradigms have been extensively used in two fields: (1) as a stimulus to produce cerebral vascular changes, and (2) to study the physiology mechanisms of the breath-holding. In embodiments of the subject invention, breath-holding can be applied to assess its clinical applicability to produce peripheral tissue oxygenation changes. Overall, breath-holding is a complex physiological phenomenon invoking many biological mechanisms to conserve oxygen for critical functions. Aside from physiological conditions (lung volume, fitness, etc.), it is also mediated by the subjects resting state (exercising/stationary) and the environment itself (dry/wet).

Research into the cardiovascular side of the response often involves assessing heart rate, oxygen and carbon dioxide gas concentrations in the lungs and blood, arterial oxygen saturation, and blood pressure. However, of particular relevance to embodiments of the subject invention is the assessment of BH-induced oxygenation changes in the peripheries. Breath-holding induces peripheral vasoconstriction in the skin and skeletal muscle, which can reduce blood flow to the skin by as much as 40%.

Figures 4A, 4B, 4C, 4D, 4E, 4F, 4G, 4H:
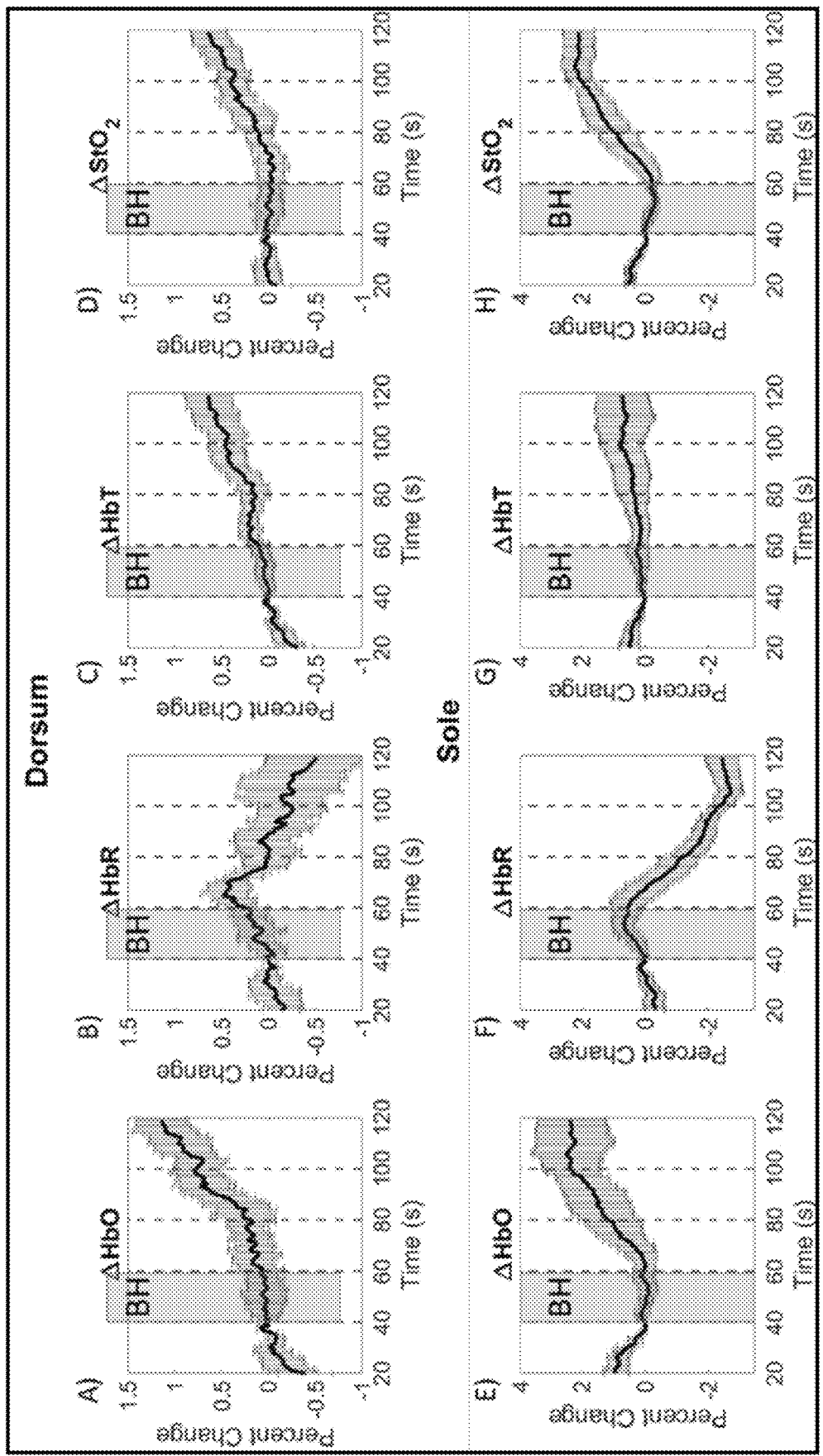
FIGS. 4A-4H show plots of percent change versus time (in s), showing average breath-hold induced hemoglobin concentration changes, calculated as the percent change from breath-hold onset, across all control subjects (and repetitions) by side of the foot for: oxy-(FIGS. 4A and 4E), deoxy- (FIGS. 4B and 4F), total hemoglobin (FIGS. 4C and 4G), and oxygen saturation (FIGS. 4D and 4H). The average signals were plotted with the standard error ((blue) vertical bars) calculated from all subjects at each timepoint. The gray shaded region denotes the breath-hold phase, and every 20 s of the post breath-hold (or recovery) phase is shown in increments as denoted by dashed vertical lines.
Figures 5A, 5B, 5C, 5D:
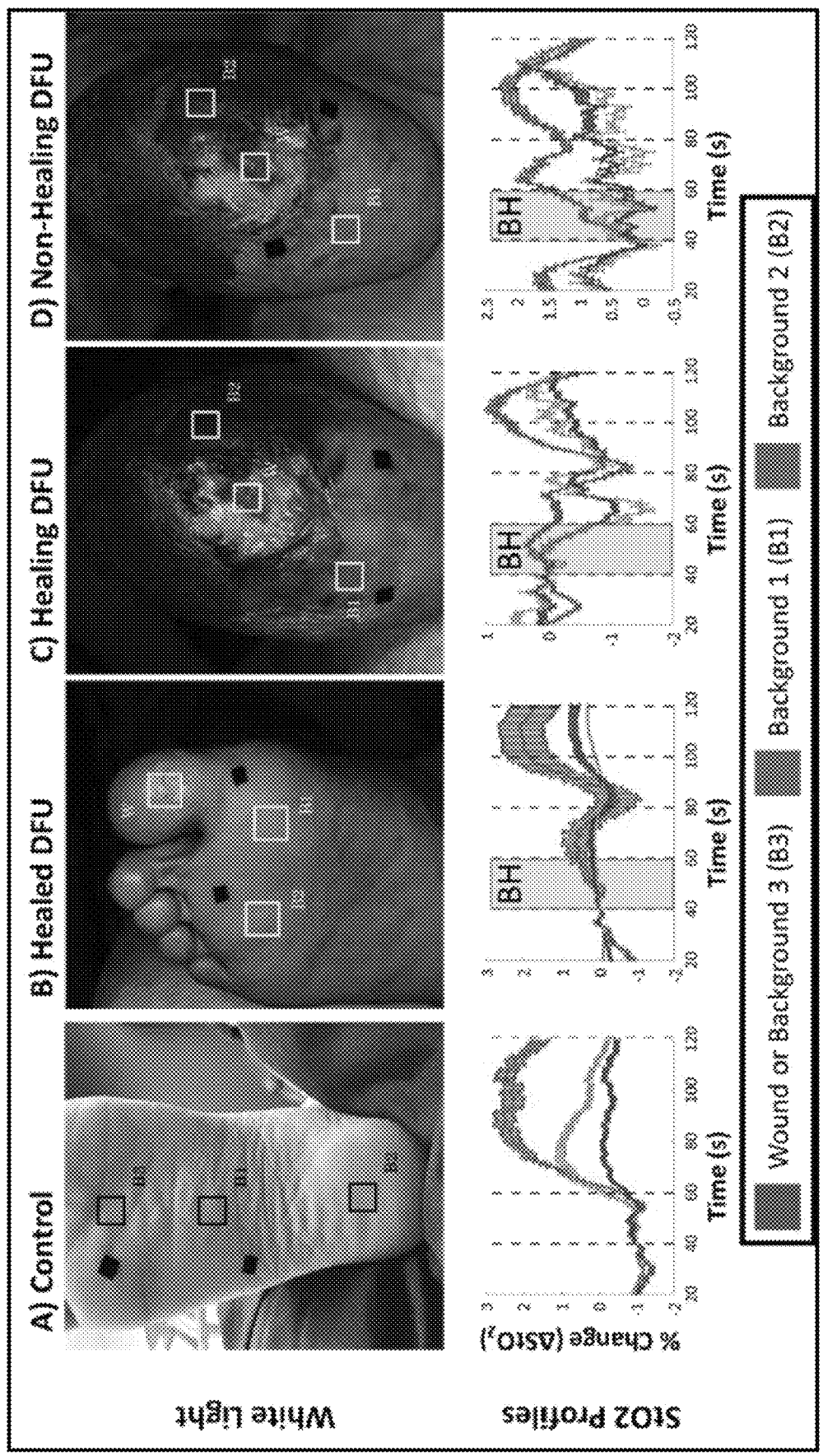
FIGS. 5A-5D show white light images and corresponding plots of percent change (change in oxygen saturation ($\Delta stO_2$)) versus time (in s) for a control case (FIG. 5A), a healed diabetic foot ulcer (DFU) from a first subject (FIG. 5B), a healing DFU (week 1) from a second subject (FIG. 5C), and a non-healing DFU (week 6) case from the second subject (FIG. 5D). The corresponding plots at the bottom show hemoglobin concentration profiles for regions of interest (ROIs) selected over the wound (W) and background (B1, B2, and B3) tissue regions as labeled in the images.
Figures 6A, 6B, 6C, 6D:
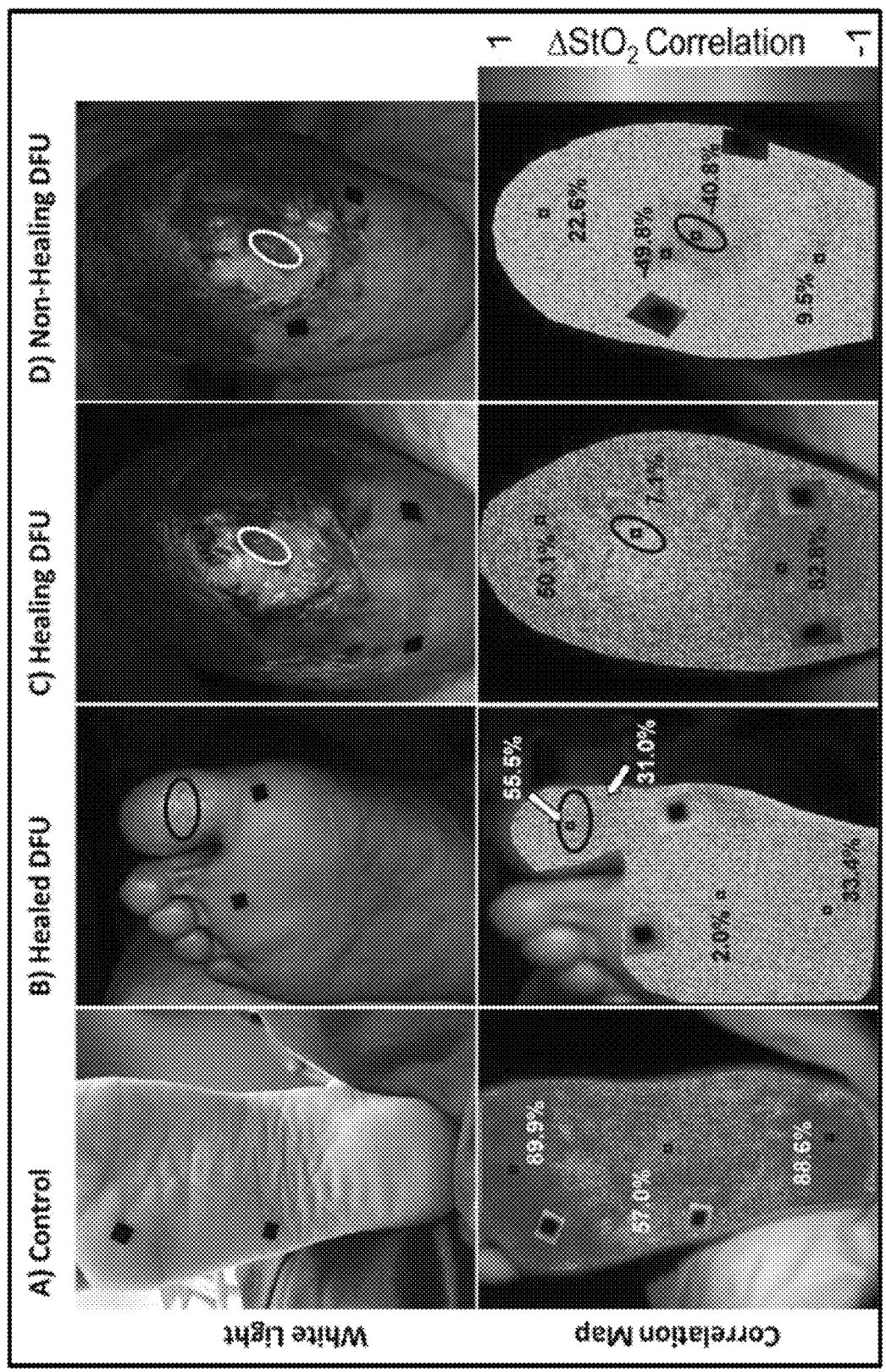
FIGS. 6A-6D show white light images and corresponding oxygen saturation-based oxygenated flow correlation maps for a control case (FIG. 6A), a healed diabetic foot ulcer (DFU) from a first subject (FIG. 6B), a healing DFU (week 1) from a second subject (FIG. 6C), and a non-healing DFU (week 6) case from the second subject (FIG. 6D). Red in the correlation maps is for regions that are positively correlated (+1), or synchronous, oxygenated flow changes with respect to the reference signal. Blue in the correlation maps is for regions that are negatively correlated (−1), or asynchronous, oxygenated flow changes with respect to the reference. The black ovals in the DFU maps denote the (former) DFU location, and the blue squares are segmented out fiducial markers used for spatial referencing.

In embodiments of the subject invention, a decrease in the oxygen saturation and an increase in deoxyhemoglobin (by the 10th second) can be observed in the sole of the foot during the breath-holding phase (as shown in FIGS. 4F and 4H). Changes in oxyhemoglobin and total hemoglobin were not as distinct during the breath-hold phase in the sole of the foot. These hemoglobin-based oxygenation changes observed in response to breath-holding are logically expected. Humans are by evolution oxygen rich creatures. As measured by pulse oximetry-based means, the normal human has a nominal oxygen saturation of 95%. Given the relatively short duration of the breath-hold phase, the change in concentration of oxyhemoglobin may have been smaller with respect to deoxyhemoglobin which would continuously build up. This in turn would affect the overall oxygen saturation. The greatest signal change was observed on the sole of the foot after breath-holding in comparison to changes observed in the dorsum of the foot.

Overall, the changes in oxygenation parameters were greater during the recovery phase than during the breath-holding phase in both the dorsum and sole of the foot (as shown in FIGS. 4A-4H). An overshoot in oxygen saturation was observed during the recovery phase. An overshoot in oxy-hemoglobin was also observed, along with an undershoot in deoxyhemoglobin. The overshoot in $\Delta HbO$, and $\Delta StO_2$ and an undershoot in $\Delta HbR$ continued until the end of the 60-s recovery phase. The total hemoglobin also increased during the 60-s recovery phase but to a lesser extent, as it is a summation of the increased oxy- and decreased deoxy-hemoglobin signal.

One potential influence that may affect the magnitude of the oxygenation changes observed during the recovery phase is how subjects resumed normal breathing. Most subjects took a deep breath during the imaging studies after being informed to resume normal breathing. Deep inspiration induces a vasoconstrictive effect in the peripheries as measured from the fingers and is mediated by the sympathetic nervous system, like breath-holding. The degree of inspiration-based vasoconstriction is not as sensitive to the duration of the inspiration, but rather the change in lung volumes. Therefore, the change in lung volume between residual volume and total lung capacity would likely illicit a strong vasoconstrictive response.

Around the 100th second time point in the paradigm, a change in oxygenation trend was observed on the sole of the foot for all hemoglobin parameters (as seen in FIGS. 4A-4H). Oxyhemoglobin and oxygen saturation concentration was observed to plateau and stabilize at a concentration about 2% greater than at breath-hold onset. The same was observed with total hemoglobin, but at a lower concentration (about 0.5% greater). Inversely, deoxyhemoglobin was observed to reach its minimum value (about 2.5% less) from baseline around the same 100th second, followed by a slight increase thereafter (as observed from FIG. 4F). The observed change in trend might indicate a return to a new baseline, given the short duration of the breath-hold phase. While trends on both sides of the foot were similar during the recovery phase from 61 s-100 s, the overall extent of oxygenation concentration changes on the dorsum was lesser than the sole. A possible reason could be due to superficial structures located on the dorsum, such as tendons and vasculature structures with varied flow patterns. Overall, the strong hemoglobin-based response post breath-hold may indicate that, for short duration breath-holds the greatest oxygenation changes may be caused by the body attempting to reach a new baseline post stimulus.

In summary, regardless of potential variations between and within subjects, a 20-s breath-hold and a 60-s recovery phase demonstrated a consistent trend in all oxygenation parameters across all subjects and repetitions in their imaged dorsum and sole of the foot.

Independent of slight variations in how each subject performed the breath-holding and relaxation, the physiological changes in these oxygenation parameters were similar. This demonstrates that the underlying phenomenon of peripheral vasoconstriction is consistent in all subjects and even upon repeated measurements. Hence, breath-hold based paradigms can serve as a potential stimulus to induce vasoconstriction in the peripheries to alter blood flow and hence assess the adequacy of tissue oxygenation below the skin. The 80-s paradigm (20-s breath-hold and 60-s recovery phase) can be further shortened to observe the same changes in response to peripheral vasoconstriction when a 40-s paradigm (20-s breath-hold and 20-s recovery phase) is applied. The increase in $\Delta HbO$ and $\Delta StO_2$ and the decrease in $\Delta HbR$ was distinctly observed even within the first 20-s of the recovery phase (as seen in FIGS. 4A-4H). Hence, the overall breath-hold paradigm can be shortened to 40-s for further oxygenation flow correlation analysis.

From the hemoglobin concentration profiles of the DFU subjects, it can be observed that oxygen saturation increased post breath-holding like controls. It can also be noted that the response to breath-holding can be more varied between the DFU cases. The variation in signal between DFUs could potentially reflect differences in how the breath-hold paradigm was performed by these subjects and possibly the differences in the imaged tissue location (post-amputee vs intact foot). In addition, the variations may be due to the extent of microcirculatory dysfunction between subjects at different stages in their treatment. DFU subjects, and diabetics as a whole, have impaired microcirculation that can be observed as early as the pre-diabetic phase.

The variation in breath-holding response may, in turn, reflect the underlying microcirculatory dysfunction. The microcirculatory impairment in diabetics may explain the asynchronous oxygenated flow response observed in the correlation maps of the non-healing DFU case.

Quantification of the differences in oxygenated flow response between healing and non-healing DFUs is the subject of ongoing work. From DFU subject 2, it was also observed that signal trend between the open DFU and background regions differed. Melanin acts as an optical absorber that increases in concentration with darker skin colors. Hence, the signal intensity of the hemoglobin-concentrations profile plots was inherently influenced by the presence of melanin. In subject 2, the darker (Grade 5) and lighter (Grade 2) ROIs were more than 88% correlated in the healing and non-healing case. This indicated that the variation in hemoglobin signal was due to variations in flow changes, and not from the contribution of melanin. While the background regions were stronger correlated in the healing and non-healing case, the wound region was only moderately correlated, between 26-57% (FIG. 8), to the background region for either case acquired from DFU subject 2. The moderate correlation between the wound and background region in the healing and non-healing case may reflect differing underlying causes; further supporting that in a temporal setting the contribution of melanin to the measured hemoglobin-based signal may be neglectable. Temporal oxygenation monitoring allowed for an intensity-independent imaging approach across different skin colors.

Controls: From the oxygenation flow correlation analysis across all control subjects, the calculated OFI from correlation maps of the sole and dorsum of the foot were positive (i.e., positively correlated). The positive tendency indicates that the oxygenated flow changes across the foot in response to breath-holding is overall synchronous (or similar). This was visually depicted in the control subject correlation map given in FIGS. 6A-6D. The OFI of the dorsum side correlation maps may partly be due to the superficial venous structures. Veins on the dorsum of the foot rank among the most superficial veins in the body. These superficial, blood-filled structures may inherently have a different oxygenated flow response when compared to the surrounding tissue that diffusively receives their oxygen from capillaries. Regardless, the overall positive OFI values calculated on either side support a synchronous oxygenated flow response to breath-holding stimulus in controls.

DFUs: The flow correlation maps between the control case and DFU subjects differed. Unlike the healed and healing DFU case, the correlation map of the non-healing DFU region indicated an asynchronous oxygenated flow (with negative correlation values) in the wound bed and its immediate surroundings. The asynchrony in and around the wound region may indicate a compromise in the oxygenated flow to the foot, thus hindering healing. Additionally, the calculated OFI for the non-healing DFU was distinctly lower than the healed and healing DFU. The lower OFI demonstrates that there is an overall reduction in the oxygenation flow to the entire imaged foot region. Hence, the OFI could be a potential indicator of adequacy of oxygenation flows in terms of flow patterns (or synchrony) to assess if the DFUs are towards healing or still remain non-healing. The potential of breath-holding as a technique to demarcate altered oxygenated flow in DFUs using OFI can be the subject of ongoing study.

Embodiments of the subject invention can use breath-holding as a stimulus to induce peripheral oxygenation changes. A non-invasive, non-contact NIROS device can be used to image BH-induced oxygenation changes in one or more patients (e.g., in the feet of one or more patients) (e.g., one or more control subjects). It can be observed from controls that the trend in hemoglobin-based oxygenation changes in response to breath-hold is consistent across repeated measurements and across all subjects. In certain embodiments, a 40-s breath-hold paradigm with a 20-s breath-hold and a 20-s post breath hold (or recovery phase) can be sufficient to induce peripheral vasoconstriction and related oxygenation changes in all subjects (e.g., in the feet of all subjects).

In addition, BH-induced oxygen saturation changes can be synchronous across patients (e.g., the feet of all patients) (e.g., across control subjects), demonstrating that the oxygenation flow or perfusion is similar or uniform.

An example case study was conducted on two DFU subjects to determine if BH-induced oxygenation changes were comparable to controls. It was observed that regardless of healing status, there was an increase in oxygen saturation after breath-hold. It was further observed that oxygenated flow changes acquired from differing skin color in the same subject were strongly correlated (>%). The breath-hold paradigms have great utility as a stimulus to assess the oxygenated flow patterns, overcoming the effects of melanin, towards assessing DFU healing status. Imaging studies on DFUs can employ this novel BH stimulus-based oxygenation measurements to determine the potential of flow correlation maps (e.g., in terms of an oxygenation flow index, OFI) as a biomarker to determine the potential for a wound to heal or not.

In addition to BH-based external stimulus to observe changes in tissue oxygenation flow patterns, embodiments of the subject invention can also use other external stimulus (e.g., measurements in response to leg elevation) that changes the blood perfusion or flow to the site of interest. These measurements can be used at discrete time points or dynamically, and this can also allow measurements independent of skin color.

The methods and processes described herein can be embodied as code and/or data. The software code and data described herein can be stored on one or more machine-readable media (e.g., computer-readable media), which may include any device or medium that can store code and/or data for use by a computer system. When a computer system and/or processor reads and executes the code and/or data stored on a computer-readable medium, the computer system and/or processor performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that are capable of storing computer-readable information/data. Computer-readable media should not be construed or interpreted to include any propagating signals. A computer-readable medium of embodiments of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

When ranges are used herein, combinations and subcombinations of ranges (e.g., subranges within the disclosed range) and specific embodiments therein are intended to be explicitly included. When the term "about" is used herein, in conjunction with a numerical value, it is understood that the value can be in a range of 95% of the value to 105% of the value, i.e. the value can be +/−5% of the stated value. For example, "about 1 kg" means from 0.95 kg to 1.05 kg.

Embodiments of the subject invention have certain aspects in common with U.S. Pat. Nos. 10,674,916, 11,464,453, and 11,471,696, all three of which are hereby incorporated by reference herein in their entireties.

A greater understanding of the embodiments of the subject invention and of their many advantages may be had from the following examples, given by way of illustration. The following examples are illustrative of some of the methods, applications, embodiments, and variants of the present invention. They are, of course, not to be considered as limiting the invention. Numerous changes and modifications can be made with respect to the invention.

Example 1

Three control subjects were recruited via written consent on an approved IRB protocol (IRB-13-0092). The recruited subjects included two females and one male subject, between the ages of 18-30 years, with a Fitzpatrick skin type of I (i.e., type I). In the example, subjects were instructed to conduct end-exhalation breath-holds.

The end-exhalation breath-hold paradigm was 120 s long and included an initial rest, 20 s of end exhalation breath-holding, and a recovery phase. An illustration of the breath-hold paradigm is given in FIG. 1.

An oxygenation flow correlation analysis was performed across control subjects as discussed above in the description. In addition, a similar analysis was performed on two patients with DFUs, as discussed above in the description. The results are shown in FIGS. 4A-4H, 5A-5D, 6A-6D, and 7-10.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein (including those in the "References" section, if present) are incorporated by reference in their entirety, including all figures and tables, to the extent they are not inconsistent with the explicit teachings of this specification.

What is claimed is:

1. A method for performing non-invasive, non-contact imaging on a subject, the method comprising:
   providing a near-infrared (NIR) optical imager comprising a light unit providing light at a first NIR wavelength, a filter configured to optically filter ambient light and allow only NIR light to pass, and an NIR-sensitive image sensor configured to detect NIR signals reflected from tissue of the subject;
   utilizing the NIR optical imager to scan tissue of the subject in a non-invasive, non-contact manner while the subject is engaged in a breath hold (BH) phase of a BH paradigm, the BH paradigm comprising an initial rest phase, the BH phase, and a recovery phase;
   acquiring spatio-temporal diffuse reflected maps based on the reflected NIR signals detected by the NIR-sensitive image sensor;
   generating dynamic maps based on the spatio-temporal diffuse reflected maps; and
   displaying, via a graphical user interface (GUI) stored on a machine-readable medium in operable communication with the NIR optical imager, the dynamic maps, the filter being a long-pass filter or a band-pass filter,
   the NIR signals that the NIR-sensitive image sensor is configured to detect comprising signals at the first NIR wavelength, and
   the dynamic maps being independent of a color of skin of the subject, a tissue curvature of the tissue of the subject, or both.

2. The method according to claim 1, the scanned tissue of the subject comprising a wound.

3. The method according to claim 2, the wound being a diabetic foot ulcer (DFU).

4. The method according to claim 2, further comprising:
   analyzing the dynamic maps; and
   determining a likelihood that the wound on the scanned tissue of the subject will heal based on a flow correlation value obtained from analyzing the dynamic maps,
   the flow correlation value being a tissue oxygenation-related correlation value or a diffuse reflectance-based correlation value, and
   the flow correlation value being independent of the color of skin of the subject, the tissue curvature of the tissue of the subject, or both.

5. The method according to claim 4, the correlation value being an oxygenation flow index (OFI) of the tissue of the subject.

6. The method according to claim 1, the light unit providing light at at least two different NIR wavelengths,
   the at least two different NIR wavelengths comprising the first NIR wavelength and a second NIR wavelength different from the first NIR wavelength, and
   the NIR signals that the NIR-sensitive image sensor is configured to detect further comprising signals at the second NIR wavelength.

7. The method according to claim 6, each of the first wavelength and the second wavelength being in a range of from 650 nanometers (nm) to 950 nm.

8. The method according to claim 6, the first wavelength being 682 nm, and the second wavelength being 826 nm.

9. The method according to claim 6, the light unit of the NIR optical imager being a light-emitting diode (LED) light unit,
   the NIR optical imager further comprising an LED driver configured to multiplex light from the LED light unit, and
   the method further comprising multiplexing the first wavelength and the second wavelength at a first temporal frequency and a second temporal frequency, respectively.

10. The method according to claim 9, the first temporal frequency being the same as the second temporal frequency, and
    the first temporal frequency being in a range of from 0.5 Hertz (Hz) to 100 Hz.

11. The method according to claim 1, the spatio-temporal diffuse reflected maps being used to generate spatio-temporal tissue oxygenation maps.

12. The method according to claim 1, the dynamic maps comprising at least one of: oxygenation flow correlation maps; and diffuse reflectance-based flow correlation maps.

13. The method according to claim 12, the dynamic maps comprising the oxygenation flow correlation maps, and
    the method further comprising calculating an OFI of the tissue of the subject based on the oxygenation flow correlation maps.

14. The method according to claim 1, the dynamic maps comprising at least one of an oxy-hemoglobin (HbO) map, a deoxy-hemoglobin (HbR) map, a total hemoglobin (HbT)

map, and an oxygen saturation ($StO_2$) map for a region of interest (ROI) of the tissue of the subject.

15. The method according to claim 14, further comprising extracting time-varying hemoglobin concentration profiles from the dynamic maps.

16. The method according to claim 1, the acquiring of the spatio-temporal diffuse reflected maps comprising:
coregistering the reflected NIR signals to minimize motion artifacts; and
using modified Beer-Lambert's Law to generate the spatio-temporal diffuse reflected maps based on the coregistered reflected NIR signals.

17. The method according to claim 1, the BH phase being an end-exhalation BH phase.

18. The method according to claim 1, the BH phase being at least 10 seconds (s), the initial rest phase being at least 20 s, and the recovery phase being at least 20 s.

19. A method for performing non-invasive, non-contact imaging on a subject, the method comprising:
providing a near-infrared (NIR) optical imager comprising a light unit providing light at at least two different NIR wavelengths, a filter configured to optically filter ambient light and allow only NIR light to pass, and an NIR-sensitive image sensor configured to detect NIR signals reflected from tissue of the subject;
utilizing the NIR optical imager to scan tissue of the subject in a non-invasive, non-contact manner while the subject is engaged in a breath hold (BH) phase of a BH paradigm, the BH paradigm comprising an initial rest phase, the BH phase, and a recovery phase, and the scanned tissue of the subject comprising a wound;
acquiring spatio-temporal diffuse reflected maps based on the reflected NIR signals detected by the NIR-sensitive image sensor;
generating dynamic maps based on the spatio-temporal diffuse reflected maps;
displaying, via a graphical user interface (GUI) stored on a machine-readable medium in operable communication with the NIR optical imager, the dynamic maps;
analyzing the dynamic maps; and
determining a likelihood that the wound on the scanned tissue of the subject will heal based on a flow correlation value obtained from analyzing the dynamic maps,
the dynamic maps being independent of a color of skin of the subject, a tissue curvature of the subject, or both,
the flow correlation value being a tissue oxygenation-related correlation value or a diffuse reflectance-based correlation value,
the flow correlation value being independent of the color of skin of the subject, the tissue curvature of the tissue of the subject, or both,
the filter being a long-pass filter or a band-pass filter,
the at least two different NIR wavelengths comprising a first NIR wavelength and a second NIR wavelength different from the first NIR wavelength,
the NIR signals that the NIR-sensitive image sensor is configured to detect comprising signals at the first NIR wavelength and the second NIR wavelength,
the dynamic maps comprising at least one of: oxygenation flow correlation maps; and diffuse reflectance-based flow correlation maps,
the acquiring of the spatio-temporal diffuse reflected maps comprising:
coregistering the reflected NIR signals to minimize motion artifacts; and
using modified Beer-Lambert's Law to generate the spatio-temporal diffuse reflected maps based on the coregistered reflected NIR signals,
each of the first wavelength and the second wavelength being in a range of from 650 nanometers (nm) to 950 nm,
the light unit of the NIR optical imager being a light-emitting diode (LED) light unit,
the NIR optical imager further comprising an LED driver configured to multiplex light from the LED light unit,
the method further comprising multiplexing the first wavelength and the second wavelength at a first temporal frequency and a second temporal frequency, respectively,
the first temporal frequency being the same as the second temporal frequency,
the first temporal frequency being in a range of from 0.5 Hertz (Hz) to 100 Hz,
the BH phase being an end-exhalation BH phase,
the BH phase being at least 10 seconds (s),
the initial rest phase being at least 20 s, and
the recovery phase being at least 20 s.

20. The method according to claim 19, the wound being a diabetic foot ulcer (DFU),
the BH phase being at least 20 s, and
the utilizing of the NIR optical imager to scan the tissue of the subject being performed while the subject is engaged in at least a portion of the recovery phase of the BH paradigm.

* * * * *